US008063076B2

(12) United States Patent
Cleary et al.

(10) Patent No.: US 8,063,076 B2
(45) Date of Patent: Nov. 22, 2011

(54) SOLID FORMS OF 2-CHLORO-4-[1-(4-FLUORO-PHENYL)-2,5-DIMETHYL-1H-IMIDAZOL-4-YLETHYNYL]-PYRIDINE

(75) Inventors: Thomas Cleary, Florence, SC (US); Alexander Glomme, Birsfelden (CH); Olaf Grassmann, Loerrach (DE); Shan-Ming Kuang, Florence, SC (US); Roland Meier, Ueken (CH); Doreen Miller, Florence, SC (US); Regina Moog, Freiburg (DE); Franziska E. Rohrer, Riehen (CH); Jason Yang, Florence, SC (US)

(73) Assignee: Hoffmann-La Roche Inc., Nutley, NJ (US)

( * ) Notice: Subject to any disclaimer, the term of this patent is extended or adjusted under 35 U.S.C. 154(b) by 969 days.

(21) Appl. No.: 11/957,515

(22) Filed: Dec. 17, 2007

(65) Prior Publication Data

US 2008/0312288 A1 Dec. 18, 2008

Related U.S. Application Data

(60) Provisional application No. 60/876,398, filed on Dec. 21, 2006.

(51) Int. Cl.
A61K 31/4439 (2006.01)
C07D 401/06 (2006.01)

(52) U.S. Cl. .................................. 514/341; 546/272.7
(58) Field of Classification Search ............... 546/272.7; 514/341
See application file for complete search history.

(56) References Cited

U.S. PATENT DOCUMENTS

| 3,303,199 | A | 2/1967 | Doebel et al. |
| 3,341,548 | A | 9/1967 | Hoffer |
| 4,352,818 | A | 10/1982 | Hunkeler et al. |
| 4,508,560 | A | 4/1985 | Brunner et al. |
| 4,711,962 | A | 12/1987 | Leone-Bay |
| 6,627,646 | B2 * | 9/2003 | Bakale et al. ............... 514/322 |
| 7,091,222 | B2 | 8/2006 | Buettelmann et al. |
| 7,153,874 | B2 | 12/2006 | Buettelmann et al. |
| 2004/0259917 | A1 | 12/2004 | Cosford et al. |

FOREIGN PATENT DOCUMENTS

| DE | 2035905 | 2/1972 |
| EP | 059 390 | 9/1982 |
| WO | WO 91/00277 | 1/1991 |
| WO | WO 99/02497 | 1/1999 |
| WO | WO 99/08678 | 2/1999 |
| WO | WO 01/16121 | 3/2001 |
| WO | WO 02/08205 | 1/2002 |
| WO | WO 02/46166 | 6/2002 |
| WO | WO 2004/080998 | 9/2004 |
| WO | WO 2004/108701 | 12/2004 |
| WO | WO 2005/003117 | 1/2005 |
| WO | WO 2005/023795 | 3/2005 |
| WO | WO 2005/118568 | 12/2005 |

OTHER PUBLICATIONS

U.S. Pharmacopia #23, National Formulary #18, 1995, 1843-1844.*
Concise Encyclopedia Chemistry, NY: Walter de Gruyter, 1993, 872-873.*
Muzaffar et al., "Polymorphism and Drug Availability, etc.," J of Pharm. (Lahore), 1979, 1(1), 59-66.*
Jain et al., "Polymorphism in Pharmacy", Indian Drugs, 1986, 23(6) 315-329.*
Taday et al., "Using Terahertz, etc.," J of Pharm. Sci., 92(4), 2003, 831-838.*
Doelker, english translation of Ann. Pharm. Fr., 2002, 60: 161-176, pp. 1-39.*
Doelker, english translation of S.T.P, Pratiques (1999), 9(5), 399-409, pp. 1-33.*
Otuska et al., "Effect of Polymorphic, etc.," Chem. Pharm. Bull., 47(6) 852-856 (1999).*
CMU Pharmaceutical polymorphism, internet, p. 1-3 (2002) (print out Apr. 3, 2008).*
Singhal et al., "Drug Polymorphism, etc.," Advanced Drug Delivery reviews 56, p. 335-347 (2004).*
Sakamoto et al., Chem. Pharm. Bull., vol. 35(2) pp. 823-828 (1987).
Miller, et al., Chem. Mater., vol. 6(7) pp. 1023-1032 (1994).
Bond et al., Synth. Commun., vol. 19, pp. 2551-2566 (1989).
Sintas et al., Journal of Labelled Compds. & Radiopharmaceuticals, 39, pp. 677-684 (1997).
Hoffer et al., J. Med. Chem., vol. 17(9) pp. 1019-1020 (1974).
Ohba et al. Chem. Pharm. Bull. vol. 42, pp. 1784-1790 (1994).
Kulkarni et al., Aust. J. Chem. vol. 40(8) pp. 1399-1413 (1987).
Vasileuskii et al., Bull. Acad. Sci. USSR Div. Chem. Sci. pp. 626-(1983).
Laronde et al., Inorg. Chim. Acta, vol. 296(1), pp. 208-221 (1999).
Shafiee et al., J. Heterocyclic Chem. vol. 33, pp. 671-673 (1996).
Shafiee et al., J. Heterocyclic Chem. vol. 35, pp. 607-610 (1998).
Ivanova et al. Chem. Heterocycl. Comp. vol. 36(2), pp. 221-222 (2000).
Wadsworth, G. H., J. Chem. Soc. vol. 57, pp. 8-12 (1890).
Cornforth et al., J. Chem. Soc. pp. 1085-1087 (1952).
Ross et al., J. Med. Chem. vol. 15(10) pp. 1035-1040 (1972).
Kiyomori et al., Tetrahedron Lett. vol. 40: pp. 2657-2660 (1999).
Tohda et al., Synthesis pp. 777-778 (1977).
Cliff et al., Synthesis pp. 681-682 (1994).
Ohira, Synth. Comm. 19: pp. 561-564 (1989).
Collman et al., Org. Lett. 2: pp. 1233-1236 (2000).
Schlaeger et al., Cytotechnology 30: pp. 71-83 (1999).
Porter et al., Br. J. Pharmacol. 128: pp. 13-20 (1999).
Millan, Progress in Neurobiology 70: pp. 83-244 (2003).
Abstract corresponding to DE 2035905 (Document B6).
Fabrizio Gasparini et al., Neuropharmacology Pergamon Press, XP001032948, vol. 38, No. 10 pp. 1493-1503 (1999).

(Continued)

Primary Examiner — Patricia Morris
(74) Attorney, Agent, or Firm — George W. Johnston; Patricia S. Rocha-Tramaloni; Kimberly J. Prior

(57) ABSTRACT

The present invention relates to the mono-sulfate salt, crystalline forms A and B of the mono-sulfate salt, an amorphous form of the mono-sulfate salt, hemi-sulfate salts, and a crystalline form A of the hemi-sulfate salt of the compound 2-chloro-4-[1-(4-fluoro-phenyl)-2,5-dimethyl-1H-imidazol-4-ylethynyl]-pyridine.

10 Claims, 11 Drawing Sheets

OTHER PUBLICATIONS

Figure 1:
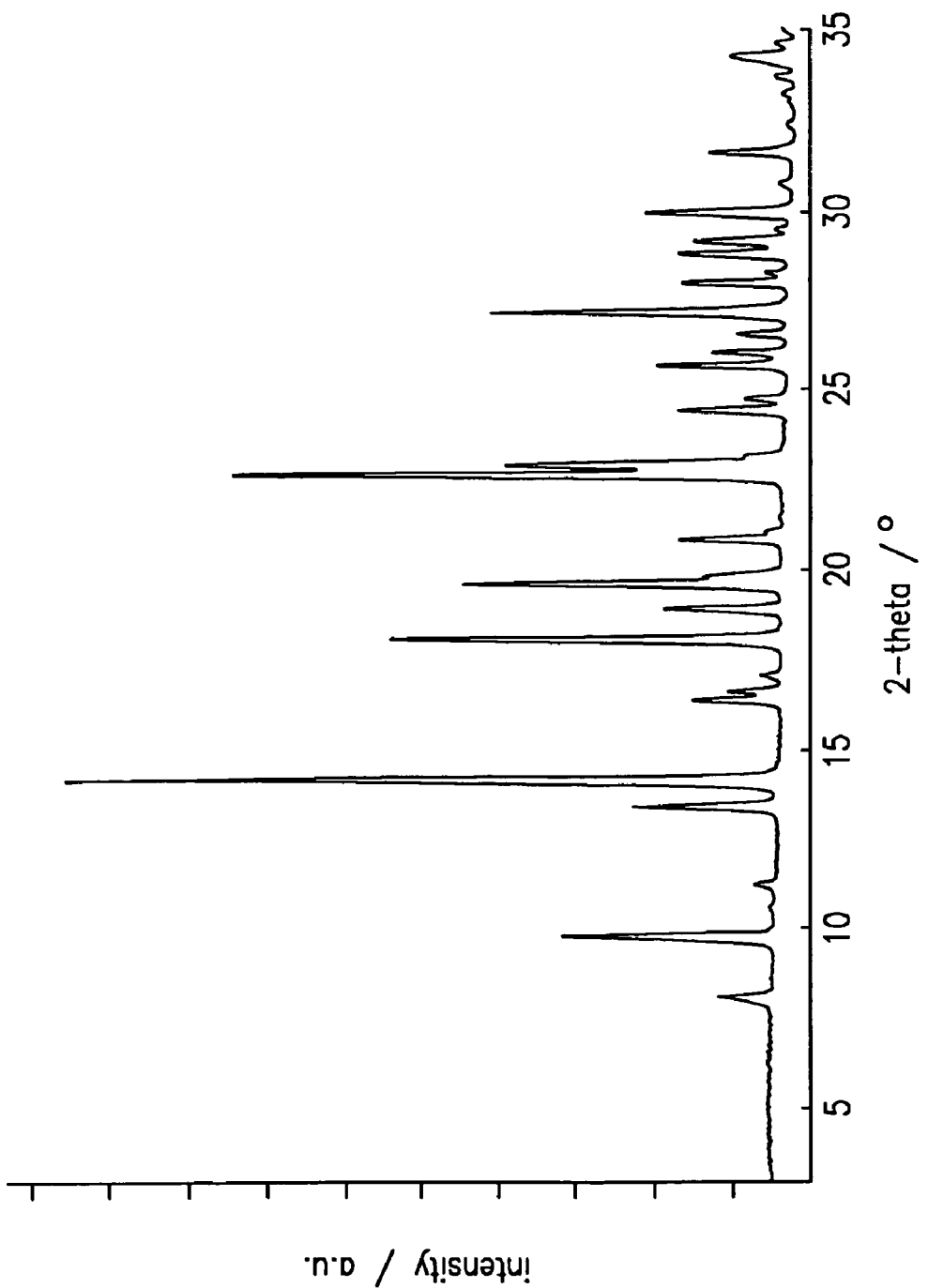

Will P.J.M. Spooren et al., Trends in Phrmacological Sciences, Elsevier Trends Journal, XP004247865, vol. 22, No. 7, pp. 331-337 (2001).
Arena, et al., Journal of Medicinal Chem. American Chem. Society, XP001005697, vol. 18, No. 11, pp. 1147-1150 (1975).
Mutel, Expert Opin. Ther. Patents, vol. 12, pp. 1845-1852 (2002).
Storto et al., European Journal of Pharmacology (2004), vol. 497(1 pp. 25-27.
Storto et al., Journal of Hepatology (2003) vol. 38(2), pp. 179-187.
Storto et al., Hepatology (Philadelphia) (2000), vol. 31(3), pp. 649 655.
Lynch, et al., Expert Opin. Ther. Patents (2002) vol. 12, pp. 11-27.

* cited by examiner

SOLID FORMS OF 2-CHLORO-4-[1-(4-FLUORO-PHENYL)-2,5-DIMETHYL-1H-IMIDAZOL-4-YLETHYNYL]-PYRIDINE

PRIORITY TO RELATED APPLICATIONS

This application claims the benefit of U.S. Provisional Application No. 60/876,398, filed Dec. 21, 2006, which is hereby incorporated by reference in its entirety.

The present invention relates to mono-sulfate and hemi-sulfate salts of 2-Chloro-4-[1-(4-fluoro-phenyl)-2,5-dimethyl-1H-imidazol-4-ylethynyl]-pyridine, to crystalline and amorphous forms thereof and to their use in pharmaceutical formulations.

2-Chloro-4-[1-(4-fluoro-phenyl)-2,5-dimethyl-1H-imidazol-4-ylethynyl]-pyridine has been already described in published PCT patent application No. WO 2004/108701.

2-Chloro-4-[1-(4-fluoro-phenyl)-2,5-dimethyl-1H-imidazol-4-ylethynyl]-pyridine has been described as active on the mGluR5 receptor for the treatment of diseases, related to this receptor, such acute and/or chronic neurological disorders, in particular anxiety, or for the treatment of chronic and acute pain, protection against liver damage, failure whether drug or disease induced, urinary incontinence, obesity, Fragile-X or Autism.

In a first aspect, the present invention relates to mono-sulfate salt and hemi-sulfate salts of the following compound:

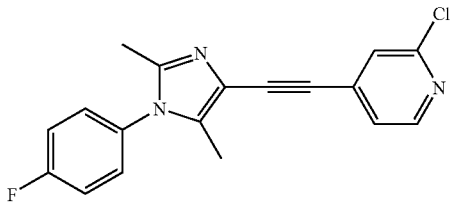

2-Chloro-4-[1-(4-fluoro-phenyl)-2,5-dimethyl-1H-imidazol-4-ylethynyl]-pyridine

In another aspect, the present invention relates to two distinct crystalline forms A and B of the mono-sulfate salt of 2-Chloro-4-[1-(4-fluoro-phenyl)-2,5-dimethyl-1H-imidazol-4-ylethynyl]-pyridine.

In yet another aspect, the present invention relates to the amorphous form of the mono-sulfate salt of 2-Chloro-4-[1-(4-fluoro-phenyl)-2,5-dimethyl-1H-imidazol-4-ylethynyl]-pyridine.

In still another aspect, the present invention relates to crystalline form A of the hemi-sulfate salt of 2-Chloro-4-[1-(4-fluoro-phenyl)-2,5-dimethyl-1H-imidazol-4-ylethynyl]-pyridine.

The aforementioned salts and their crystalline and amorphous forms can be distinguished by physical and chemical properties that can be characterized by infrared spectra, X-ray powder diffraction patterns, melting behavior or glass transition temperatures.

The present invention also provides pharmaceutical compositions containing the abovementioned salts, crystalline or amorphous forms, and a pharmaceutically acceptable carrier.

In accordance with the invention the abovementioned salts, crystalline or amorphous forms can be used for the preparation of medicaments useful in the control or prevention of illnesses based on the mGluR5 receptor. Such illnesses include acute and/or chronic neurological disorders, in particular anxiety, or for the treatment of chronic and acute pain, protection against liver damage, failure whether drug or disease induced, urinary incontinence, obesity, Fragile-X or Autism.

FIG. 1: shows an XRPD (X-Ray Powder Diffraction, STOE diffractometer) pattern of a typical lot of form A of the mono-sulfate salt of 2-Chloro-4-[1-(4-fluoro-phenyl)-2,5-dimethyl-1H-imidazol-4-ylethynyl]-pyridine.

Figure 2:
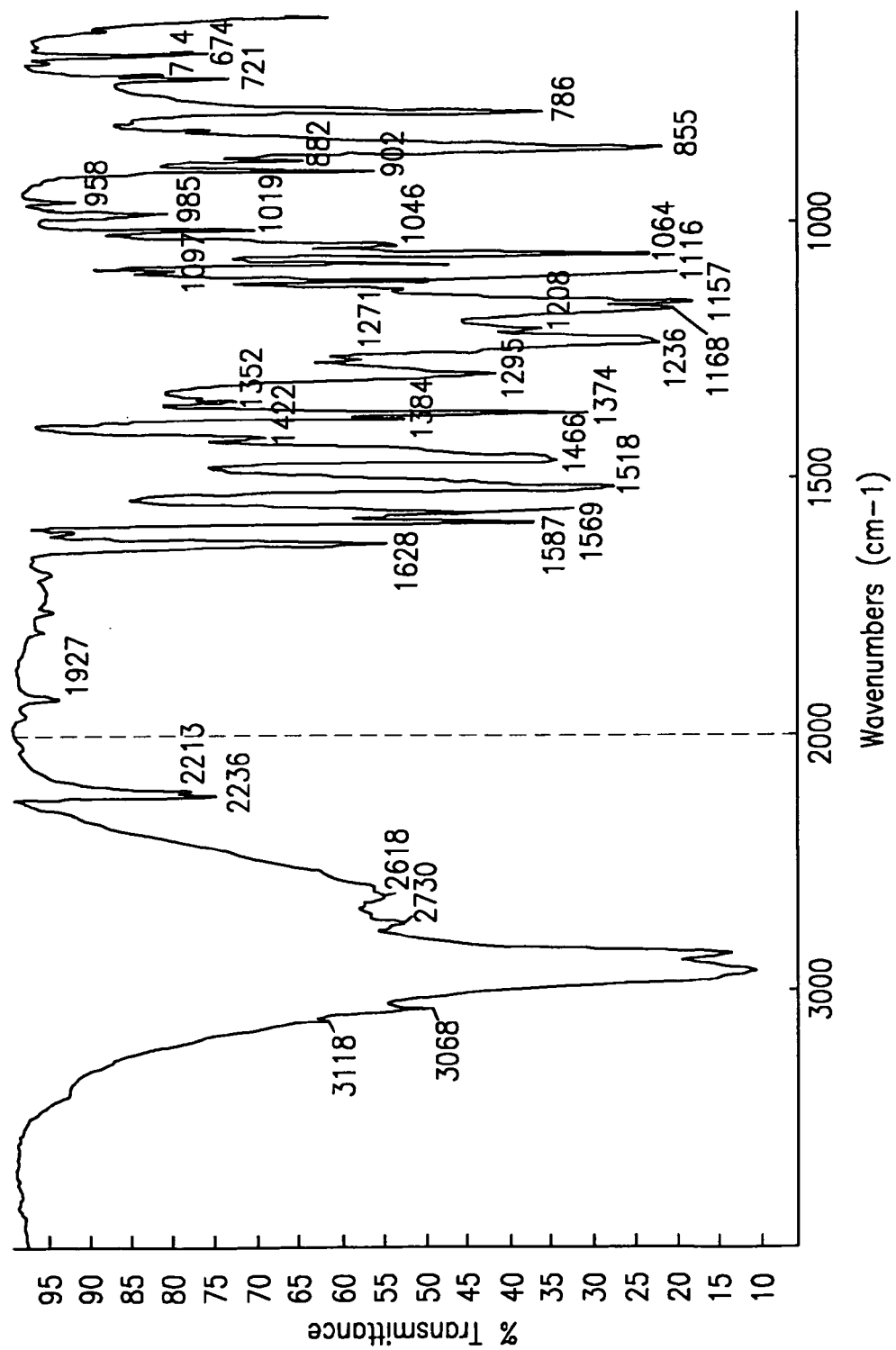

FIG. 2: shows an IR (InfraRed spectroscopy, Nicolet spectrometer) spectrum of a typical lot of form A of the mono-sulfate salt of 2-Chloro-4-[1-(4-fluoro-phenyl)-2,5-dimethyl-1H-imidazol-4-ylethynyl]-pyridine.

Figure 3:
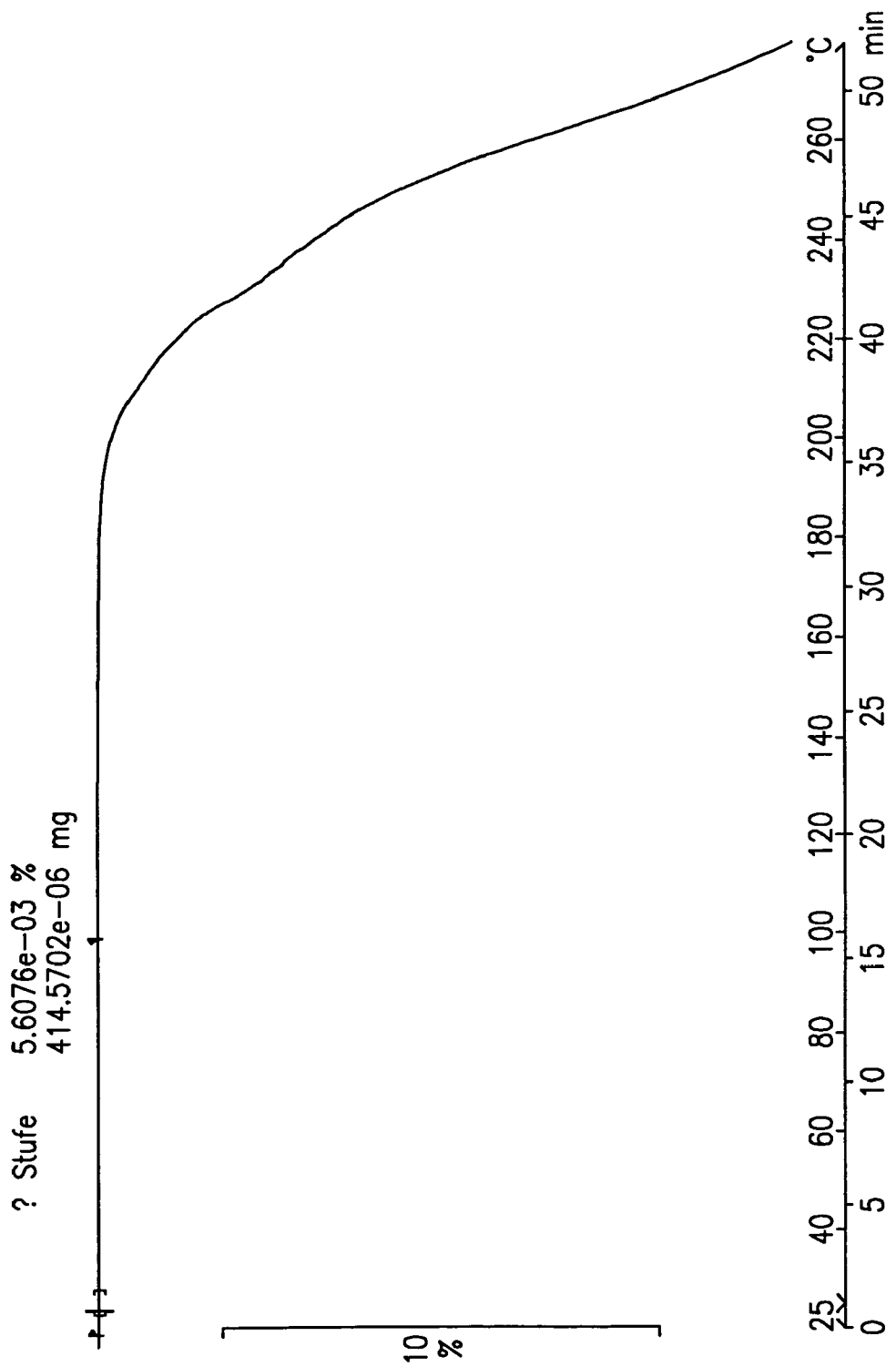

FIG. 3: shows a TGA (Thermo Gravimetric Analysis, Mettler-Toledo system) curve of a typical lot of form A of the mono-sulfate salt of 2-Chloro-4-[1-(4-fluoro-phenyl)-2,5-dimethyl-1H-imidazol-4-ylethynyl]-pyridine.

Figure 4:
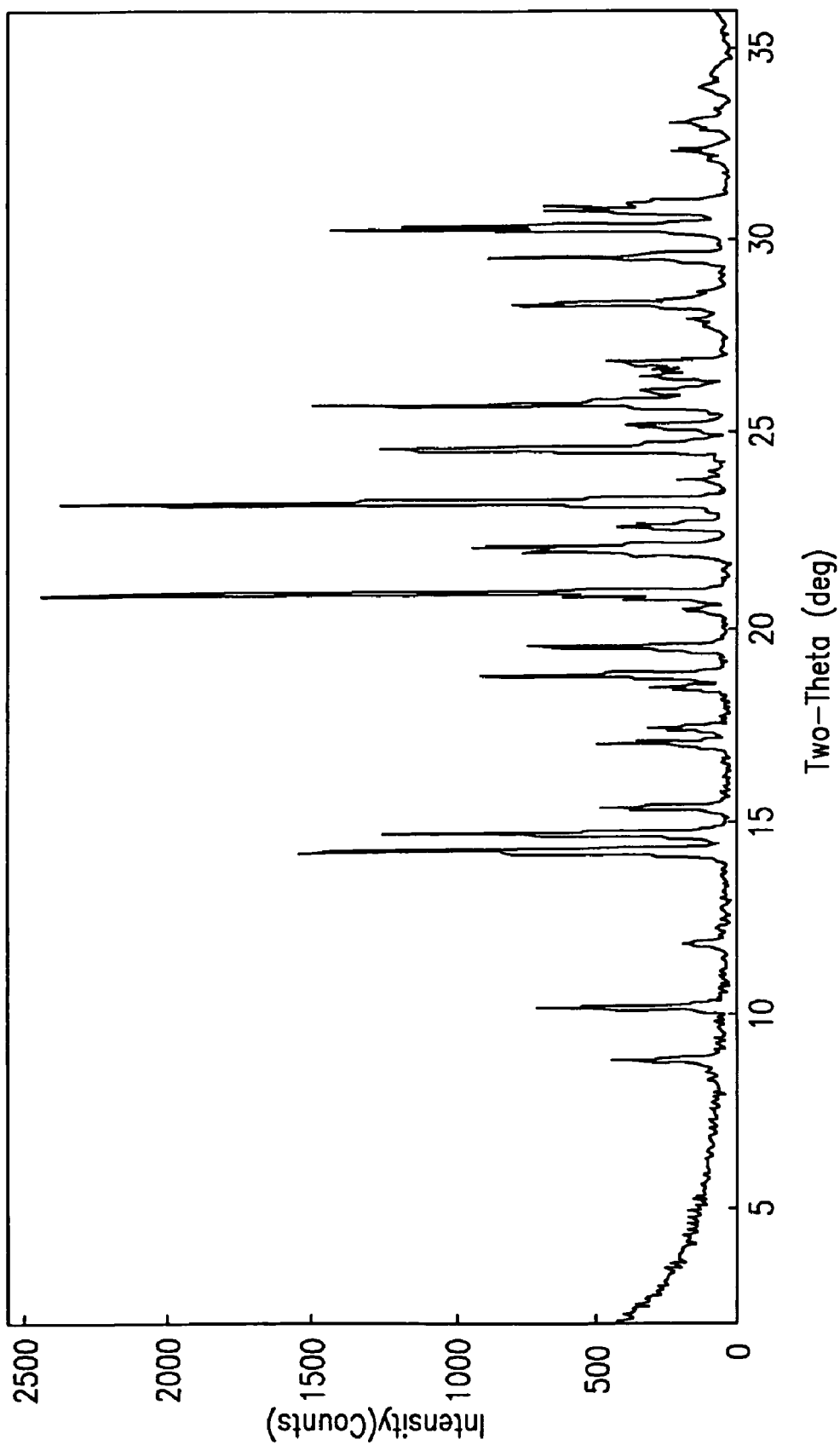

FIG. 4: shows an XRPD (X-Ray Powder Diffraction, Scintag diffractometer) pattern of a typical lot of form B of the mono-sulfate salt of 2-Chloro-4-[1-(4-fluoro-phenyl)-2,5-dimethyl-1H-imidazol-4-ylethynyl]-pyridine.

Figure 5:
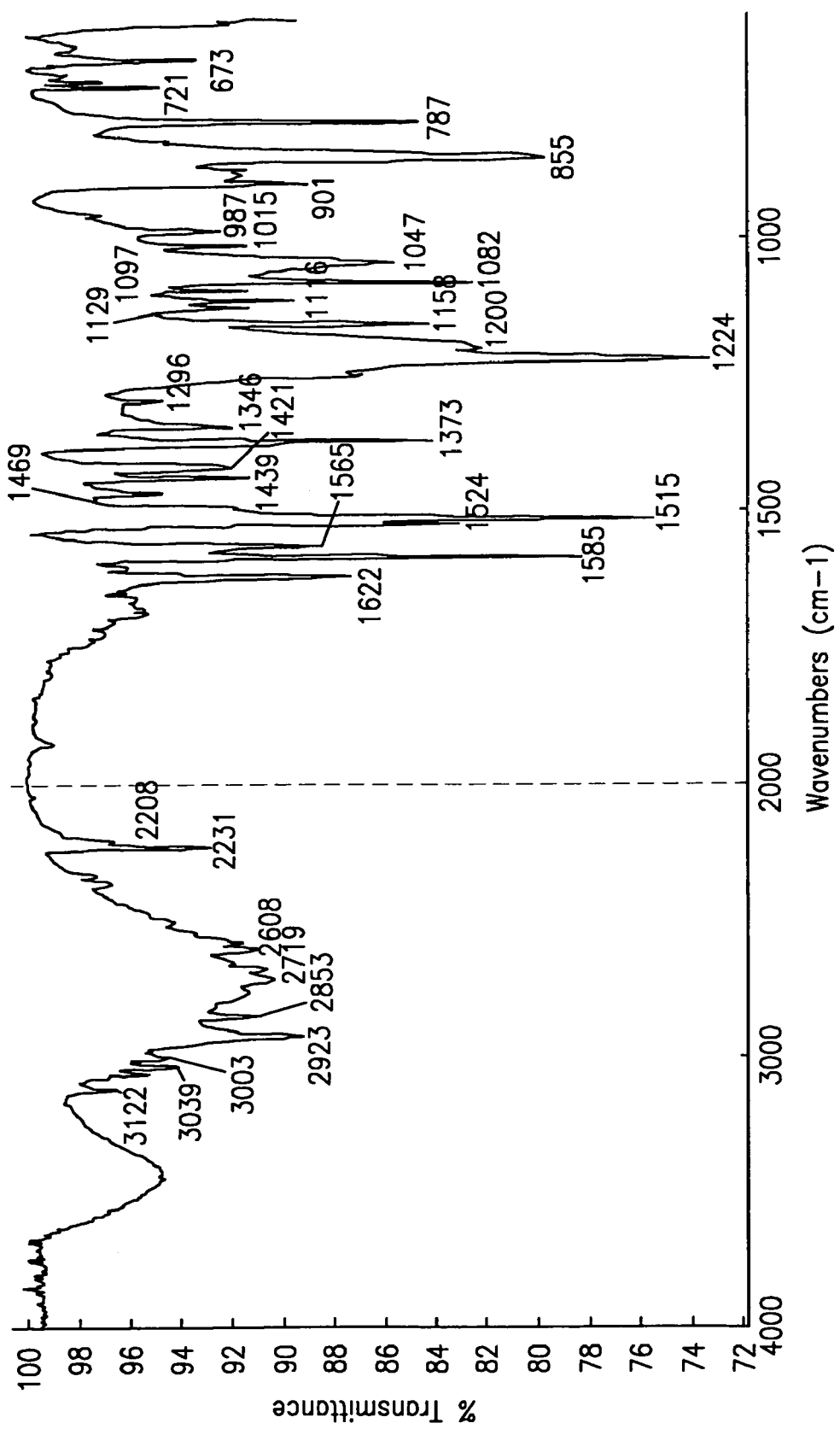

FIG. 5: shows an IR (Infra Red spectroscopy, Mattson spectrometer) spectrum of a typical lot of form B of the mono-sulfate salt of 2-Chloro-4-[1-(4-fluoro-phenyl)-2,5-dimethyl-1H-imidazol-4-ylethynyl]-pyridine.

Figure 6:
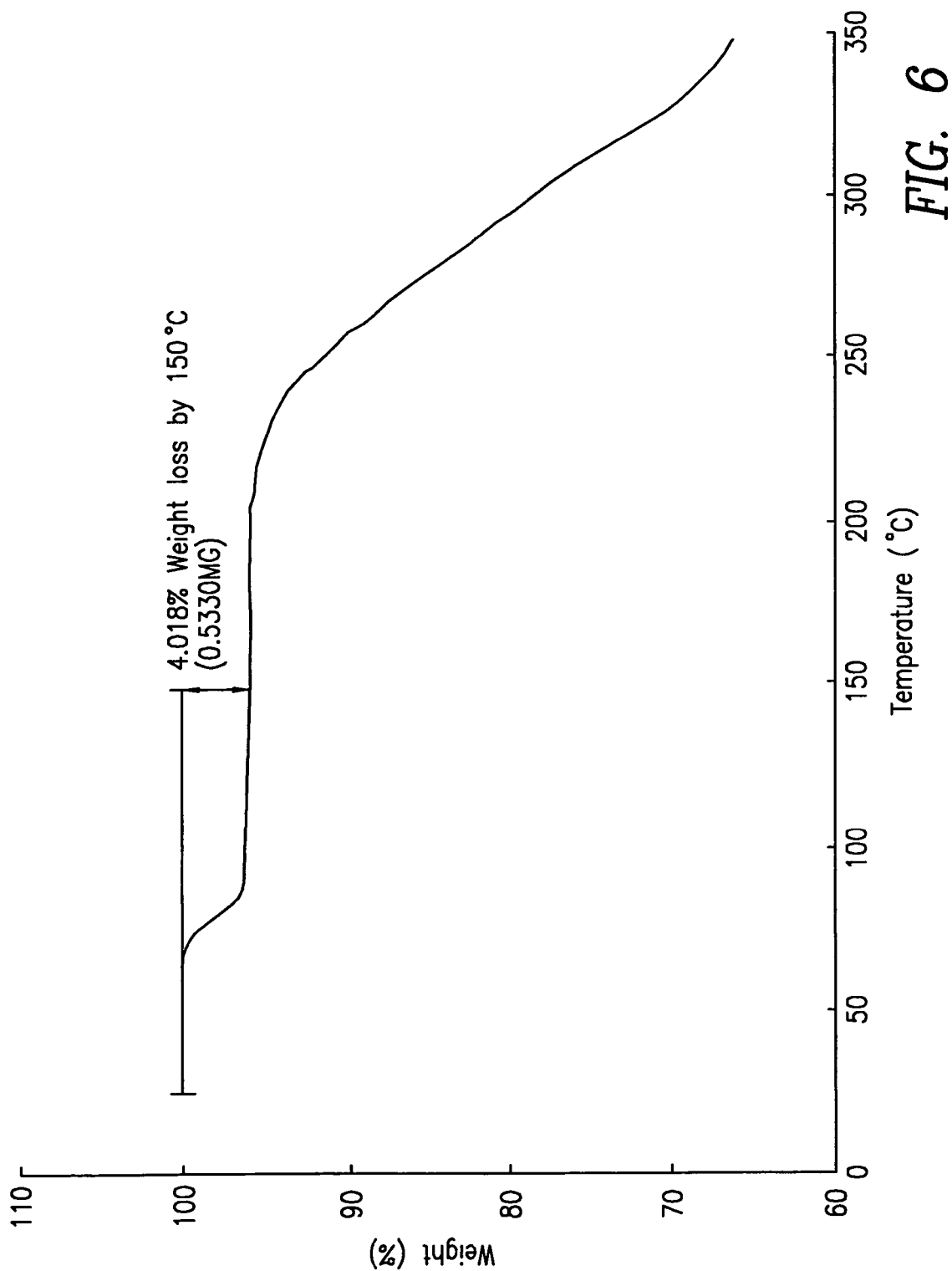
Figure 7:
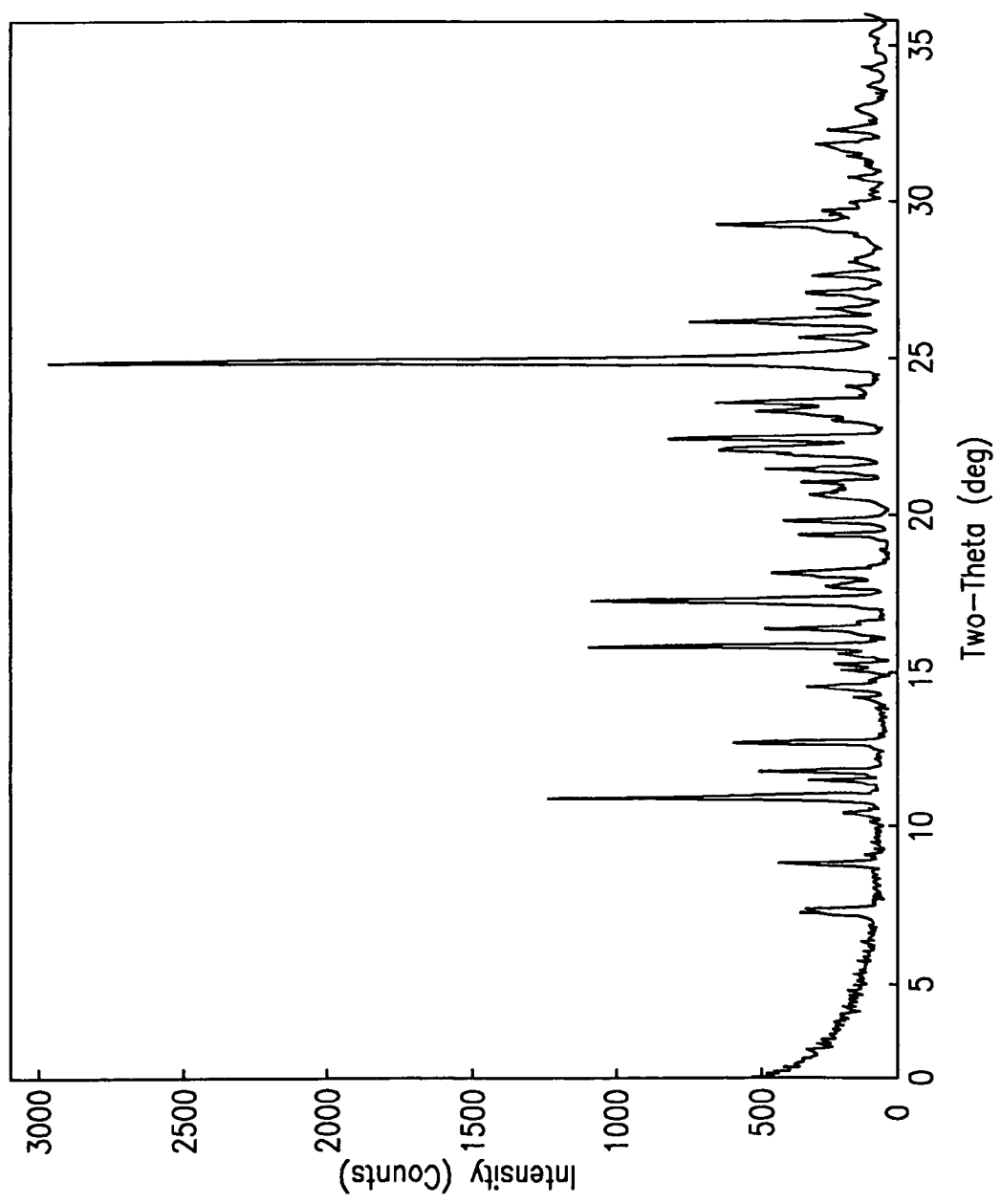

FIG. 6: shows a TGA (Thermo Gravimetric Analysis, TA Instruments system) curve of a typical lot of form B of the mono-sulfate salt of 2-Chloro-4-[1-(4-fluoro-phenyl)-2,5-dimethyl-1H-imidazol-4-ylethynyl]-pyridine FIG. 7: shows an XRPD (X-Ray Powder Diffraction, Scintag diffractometer) pattern of a typical lot of form A of the hemi-sulfate salt of 2-Chloro-4-[1-(4-fluoro-phenyl)-2,5-dimethyl-1H-imidazol-4-ylethynyl]-pyridine.

Figure 8:
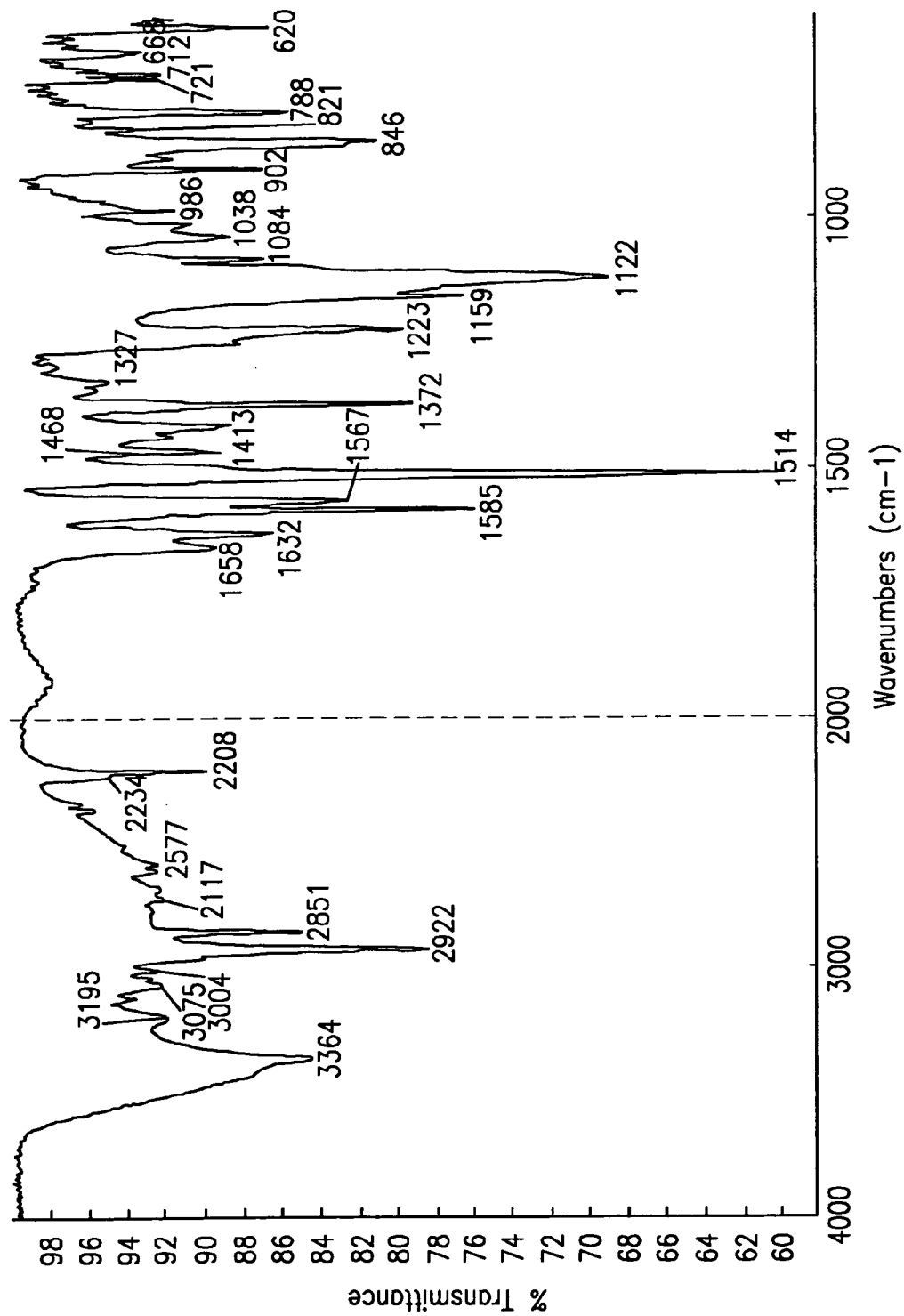

FIG. 8: shows an IR (Infra Red spectroscopy, Mattson spectrometer) spectrum of a typical lot of form A of the hemi-sulfate salt of 2-Chloro-4-[1-(4-fluoro-phenyl)-2,5-dimethyl-1H-imidazol-4-ylethynyl]-pyridine.

Figure 9:
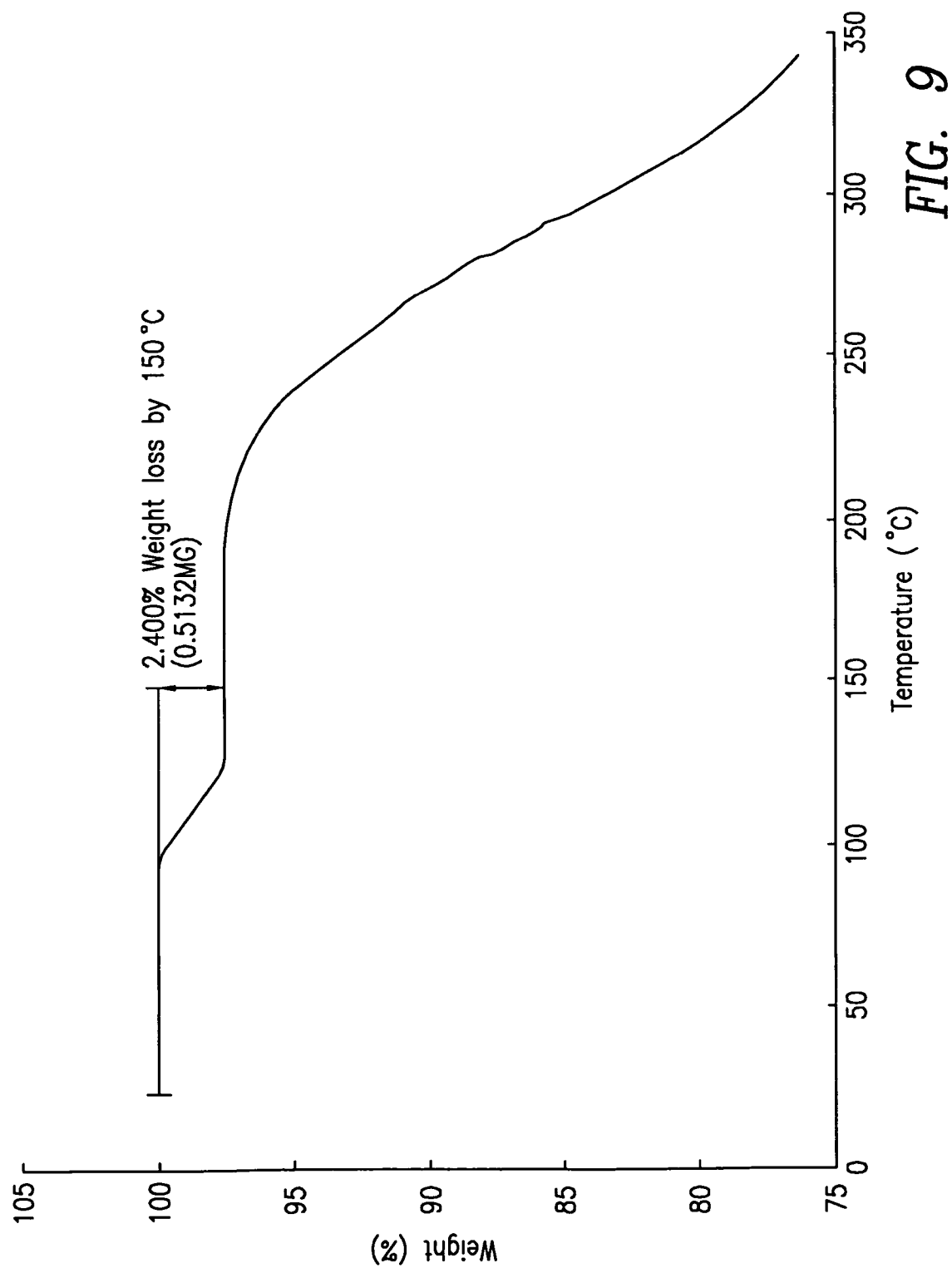

FIG. 9: shows a TGA (Thermo Gravimetric Analysis, TA Instruments system) curve of a typical lot of form A of the hemi-sulfate salt of 2-Chloro-4-[1-(4-fluoro-phenyl)-2,5-dimethyl-1H-imidazol-4-ylethynyl]-pyridine.

Figure 10:
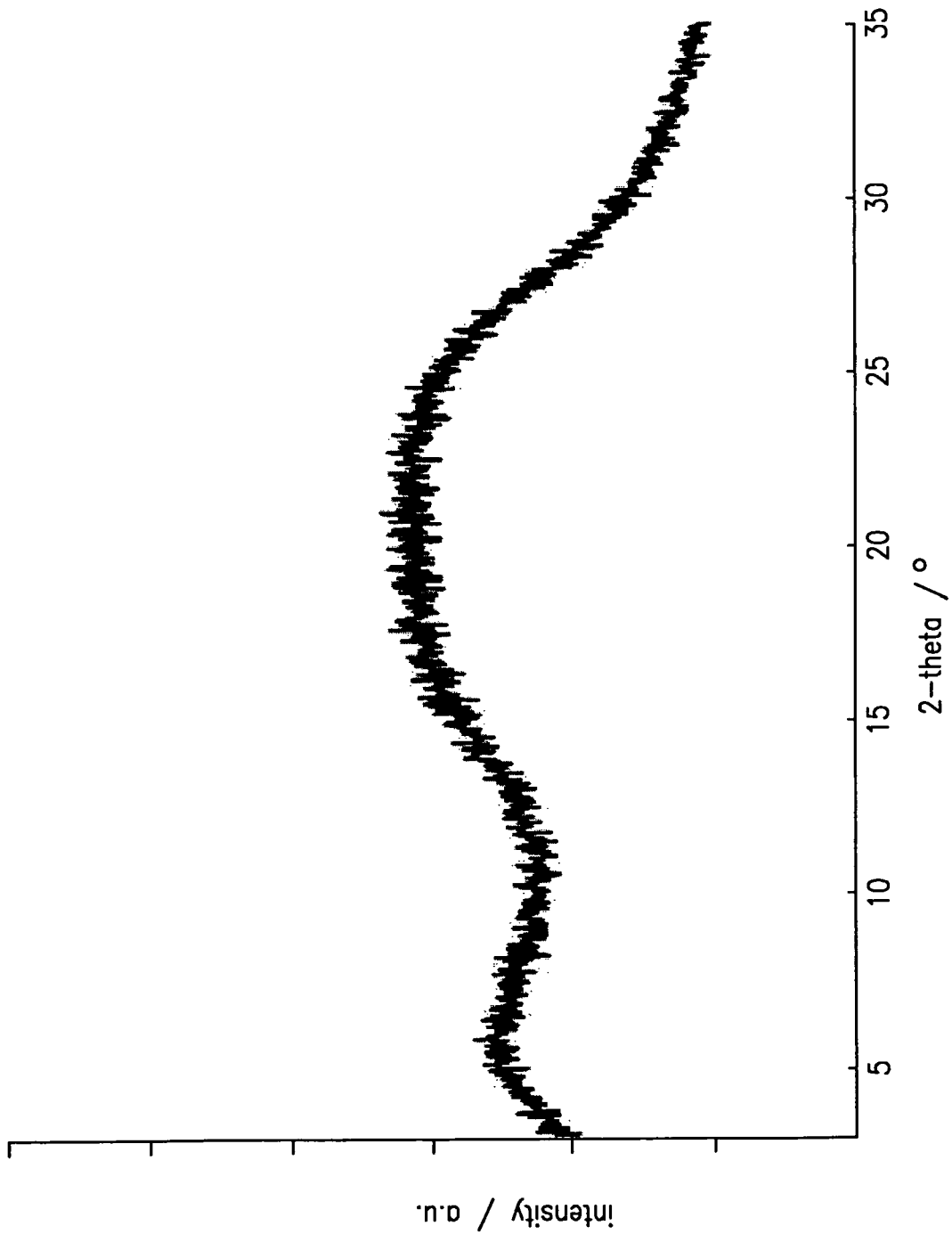

FIG. 10: shows an XRPD (X-Ray Powder Diffraction, STOE diffractometer) pattern of a typical lot of the amorphous form of the mono-sulfate salt of 2-Chloro-4-[1-(4-fluoro-phenyl)-2,5-dimethyl-1H-imidazol-4-ylethynyl]-pyridine.

Figure 11:
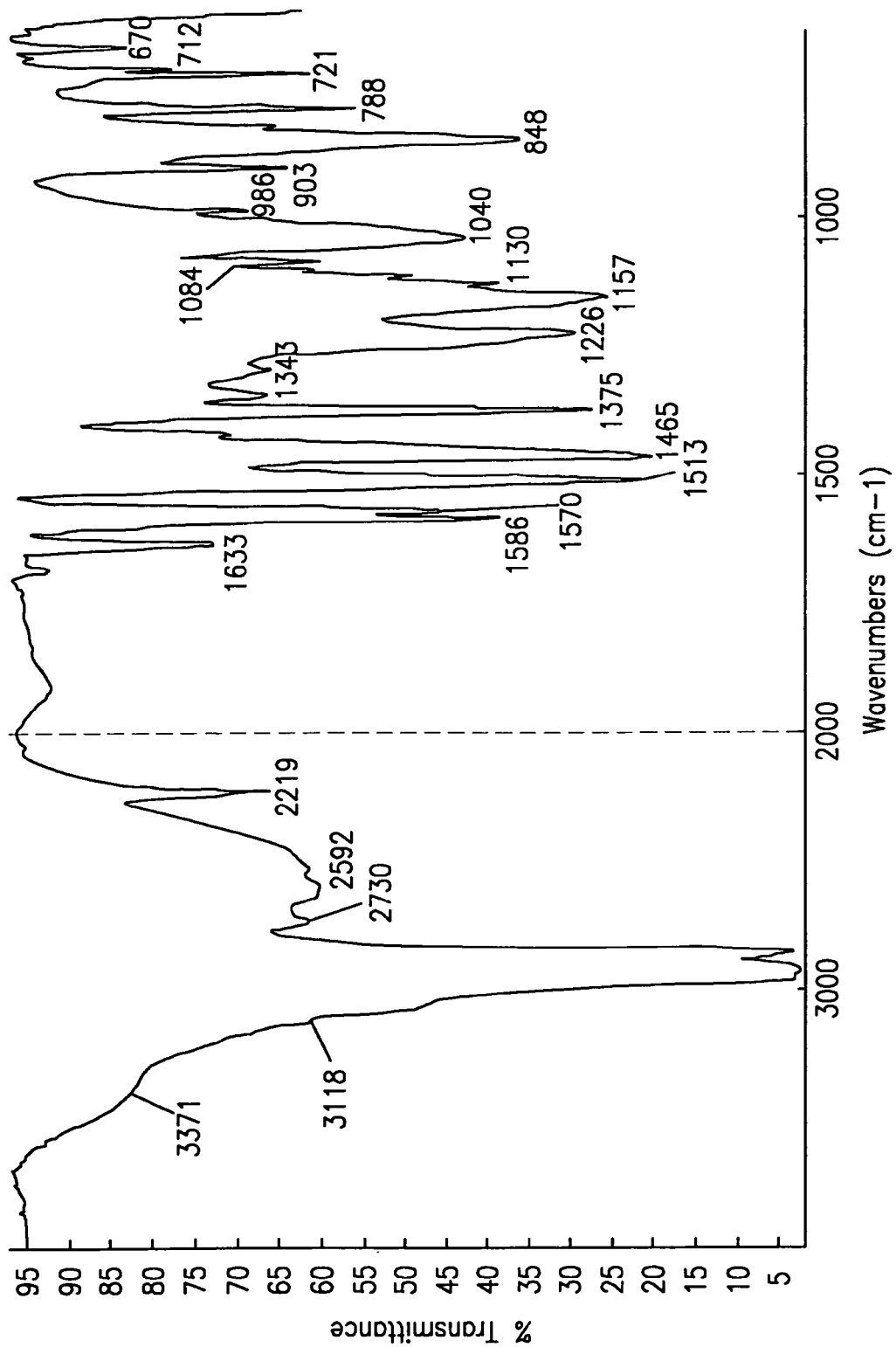

FIG. 11: shows an IR (Infra Red spectroscopy, Nicolet spectrometer) spectrum of a typical lot of the amorphous form of the mono-sulfate salt of 2-Chloro-4-[1-(4-fluoro-phenyl)-2,5-dimethyl-1H-imidazol-4-ylethynyl]-pyridine.

As used herein, "Amorphous forms" denote a material that lacks long range order and as such does not show sharp X-ray peaks. The XRPD pattern of an amorphous material is characterized by one or more amorphous halos.

"Amorphous form of the mono-sulfate salt" is used herein as abbreviation of the amorphous form of the mono-sulfate salt of 2-Chloro-4-[1-(4-fluoro-phenyl)-2,5-dimethyl-1H-imidazol-4-ylethynyl]-pyridine.

"API" is used herein as an acronym of active pharmaceutical ingredient.

"Form A of the mono-sulfate salt" is used herein as abbreviations for the crystalline form A of the mono-sulfate salt of 2-Chloro-4-[1-(4-fluoro-phenyl)-2,5-dimethyl-1H-imidazol-4-ylethynyl]-pyridine.

"Form A of the hemi-sulfate salt" is used herein as abbreviations for the crystalline form A of the hemi-sulfate salt of 2-Chloro-4-[1-(4-fluoro-phenyl)-2,5-dimethyl-1H-imidazol-4-ylethynyl]-pyridine.

"Form B of the mono-sulfate salt" is used herein as abbreviations for the crystalline form B of the mono-sulfate salt of 2-Chloro-4-[1-(4-fluoro-phenyl)-2,5-dimethyl-1H-imidazol-4-ylethynyl]-pyridine.

"Free base" is used herein as the abbreviation of the free base of 2-Chloro-4-[1-(4-fluoro-phenyl)-2,5-dimethyl-1H-imidazol-4-ylethynyl]-pyridine.

"IPA" is used herein as an acronym of 2-propanol.

'ACN' is used herein as an acronym of acetonitrile.

"IR" is used herein as an acronym of Infra Red spectroscopy. IR spectra were recorded as film of a Nujol suspension of approximately 5 mg of sample and few Nujol between two sodium chloride plates, with an FTIR spectrometer in transmittance. The Spectrometer is a Nicolet™ 20SXB or equivalent (resolution 2 cm$^{-1}$, 32 or more coadded scans, MCT detector).

Alternatively, IR was recorded as KBr disc with approximately 0.6 mg of sample and 160 mg of KBr. In this case, the Spectrometer is a Mattson Galaxy 5000 FTIR system (resolution 2 cm$^{-1}$, 32 or more coadded scans).

"Pharmaceutically acceptable" such as pharmaceutically acceptable carrier, excipient, preservatives, solubilizers, stabilizers, wetting agents, emulsifiers, sweeteners, colorants, flavoring agents, salts for varying the osmotic pressure, buffers, masking agents or antioxidants, etc., means pharmacologically acceptable and substantially non-toxic to the subject to which the particular compound is administered.

"XRPD" is used herein as an acronym of X-Ray Powder Diffraction. X-ray diffraction patterns were recorded at ambient conditions in transmission geometry with a STOE STADI P diffractometer (Cu Kα radiation, primary monochromator, position sensitive detector, angular range 3° to 42° 2 Theta, approximately 60 minutes total measurement time). The samples were prepared and analyzed without further processing (e.g. grinding or sieving) of the substance.

Alternatively, X-ray diffraction patterns were measured on a Scintag X1 powder X-ray diffractometer equipped with a sealed copper Kα1 radiation source. The samples were scanned from 2° to 36° 2θ at a rate of 1° per minute with incident beam slit widths of 2 and 4 mm and diffracted beam slit widths of 0.3 and 0.2 mm.

For single crystal structure analysis a single crystal was mounted in a loop on a goniometer and measured at ambient conditions. Alternatively, the crystal was cooled in a nitrogen stream during measurement. Data were collected on a STOE Imaging Plate Diffraction System (IPDS) from STOE (Darmstadt). In this case Mo-radiation of 0.71 Å wavelength was used for data collection. Data was processed with STOE IPDS-software. The crystal structure was solved and refined with standard crystallographic software. In this case the program ShelXTL from Bruker AXS (Karlsruhe) was used.

Alternatively, single crystal X-ray diffraction intensity data were measured at ambient conditions on a Bruker SMART APEX™ diffractometer (Mo Kα radiation, λ=0.71 Å). Raw area detector data frame integration was performed with the following softwares: SMART™ Version 5.630, SAINT™+Version 6.45 and SADABS™ Version 2.10. Bruker Analytical X-ray Systems, Inc., Madison, Wis., USA, 2003. Direct methods structure solution, difference Fourier calculations and full-matrix least-squares refinement against $F^2$ were performed according to Sheldrick, G. M. SHELXTL™ Version 6.14; Bruker Analytical X-ray Systems, Inc., Madison, Wis., USA, 2000.

"TGA" is used herein as an acronym of ThermoGravimetric Analysis. TGA curves were measured on a Mettler-Toledo™ thermogravimetric analyzer (TGA850/SDTA). System suitability tests and calibrations were carried out according to the internal standard operation procedure.

For the thermogravimetric analyses, approx. 5-10 mg of sample were placed in aluminum pans, accurately weighed and hermetically closed with perforation lids. Prior to measurement, the lids were automatically pierced resulting in approx. 1.5 mm pin holes. The samples were then heated under a flow of nitrogen of about 50 mL/min using a heating rate of 5 K/min up to 280° C.

Alternatively, thermogravimetric analysis was conducted using a Hi-Res 2950 TGA from TA Instruments. The heating rate was 10° C./min with a nitrogen purge maintained throughout the run.

"Therapeutically effective amount" means an amount that is effective to prevent, alleviate or ameliorate symptoms of disease or prolong the survival of the subject being treated.

Pharmaceutical compositions of the invention, in addition to one of the salts, crystalline or amorphous forms according to the invention mentioned hereinabove, can contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the solutions include, for example, water, polyols, sucrose, invert sugar, glucose, and the like The preparation of the free base 2-Chloro-4-[1-(4-fluoro-phenyl)-2,5-dimethyl-1H-imidazol-4-ylethynyl]-pyridine has been already described in published PCT patent applications Nos. WO 2004/108701, the content of which is incorporated by reference herein.

As already mentioned hereinabove, the present invention relates to novel salts and to crystalline and an amorphous form of these salts of the following compound:

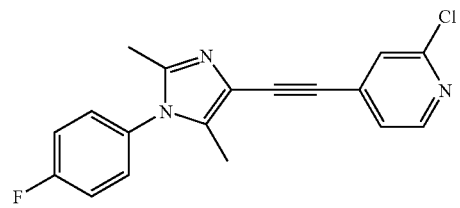

2-Chloro-4-[1-(4-fluoro-phenyl)-2,5-dimethyl-1H-imidazol-4-ylethynyl]-pyridine

It has been found that 2-Chloro-4-[1-(4-fluoro-phenyl)-2,5-dimethyl-1H-imidazol-4-ylethynyl]-pyridine can be isolated, depending upon the method of preparation, as a mono-sulfate or as a hemi-sulfate salt.

Form A and form B of the mono-sulfate salt as well as an amorphous form can be isolated from the mono-sulfate salt of 2-Chloro-4-[1-(4-fluoro-phenyl)-2,5-dimethyl-1H-imidazol-4-ylethynyl]-pyridine.

Form A of the hemi-sulfate salt can be obtained for the hemi-sulfate salt of 2-Chloro-4-[1-(4-fluoro-phenyl)-2,5-dimethyl-1H-imidazol-4-ylethynyl]-pyridine.

The mono-sulfate salt of 2-Chloro-4-[1-(4-fluoro-phenyl)-2,5-dimethyl-1H-imidazol-4-ylethynyl]-pyridine can be prepared by salt formation of 2-Chloro-4-[1-(4-fluoro-phenyl)-2,5-dimethyl-1H-imidazol-4-ylethynyl]-pyridine with sulfuric acid in 2-propanol with subsequent spontaneous precipitation.

Form A of the mono-sulfate salt of the 2-Chloro-4-[1-(4-fluoro-phenyl)-2,5-dimethyl-1H-imidazol-4-ylethynyl]-pyridine is a solvent-free, crystalline form.

Form A of the mono-sulfate salt can be obtained by salt formation of 2-Chloro-4-[1-(4-fluoro-phenyl)-2,5-dimethyl-1H-imidazol-4-ylethynyl]-pyridine with sulfuric acid in 2-propanol with subsequent spontaneous precipitation or by re-crystallization of form A of the mono-sulfate salt in solvents comprising but not limited to ACN, ACN/water, methanol, ethanol, IPA, acetic acid, 1-octanol, IPA/49% sulfuric acid (10:1, v/v).

Form A of the mono-sulfate salt can be characterized by at least three peaks selected from the following X-ray diffraction peaks obtained with a $Cu_{K\alpha}$ radiation at 2θ (2 Theta)=9.8, 13.4, 14.2, 18.1, 18.9, 19.6, 22.6, 22.9, 25.7, 27.1 and 29.9 (±0.2°).

Form A of the mono-sulfate salt can also be characterized by the following X-ray diffraction peaks obtained with a $Cu_{K\alpha}$ radiation at 2θ (2 Theta)=9.8, 13.4, 14.2, 18.1, 18.9, 19.6, 22.6, 22.9, 25.7, 27.1 and 29.9 (±0.2°).

Form A of the mono-sulfate salt can also be characterized by the X-ray powder diffraction pattern shown on FIG. 1.

Form A of the mono-sulfate salt can also be characterized by an infrared spectrum having sharp bands at 3068, 2730, 2618, 2236, 2213, 1628, 1587, 1569, 1518, 1384, 1374, 1295, 1236, 1168, 1157, 1116, 1064, 1019, 902, 855, 786 and 674 $cm^{-1}$ (±3 $cm^{-1}$).

Form A of the mono-sulfate salt can also be characterized by the infrared spectrum shown on FIG. 2.

Form A of the mono-sulfate salt is a solvent-free form as no significant weight loss is observed in the TGA curve prior to decomposition as shown on FIG. 3.

As already mentioned hereinabove, all these characteristics are shown on FIGS. 1 to 3 hereinafter.

A single crystal X-ray analysis of form A of the mono-sulfate salt was conducted. Table 1 lists as an example some crystal structure data. Crystal form A of the mono-sulfate salt was found to be an anhydrate form of mono-sulfate salt as determined by single crystal analysis. The experimental XRPD pattern collected with the form A of the mono-sulfate salt obtained is in excellent agreement with the simulated pattern calculated with atomic coordinates from single crystalline structure analysis, indicating that form A of the mono-sulfate salt was a pure crystalline phase. In the structure of form A of the mono-sulfate salt, the fluoro-benzene ring is almost perpendicular to the imidazole ring as indicated by a dihedral angle of 90.7°. A hydroxyl group of a bisulfate anion forms an intermolecular hydrogen bond with an oxygen atom of a neighboring bisulfate anion. This bisulfate anion also serves as a hydrogen bond acceptor from a protonated imidazole nitrogen atom.

Form B of the mono-sulfate salt is a mono-hydrate crystalline form.

Form B of the mono-sulfate salt can be obtained by solvent equilibration of form A of the mono-sulfate salt in IPA/water (e.g. 3:1 v/v). Form B of the mono-sulfate salt can also be prepared by re-crystallization of form A of the mono-sulfate salt in IPA/water (e.g. 3:1 v/v). Form B of the mono-sulfate salt can further be obtained upon digestion of form A of the mono-sulfate salt in e.g. aqueous sulfuric acid.

Form B of the mono-sulfate salt can be characterized by at least three peaks selected from the following X-ray diffraction peaks obtained with a $Cu_{K\alpha}$ radiation at 2θ (2 Theta)=8.9, 10.2, 14.3, 14.7, 15.4, 17.1, 18.8, 19.5, 20.9, 22.5 and 23.8 (±0.2°).

Form B of the mono-sulfate salt can also be characterized by the following X-ray diffraction peaks obtained with a $Cu_{K\alpha}$ radiation at 2θ (2 Theta)=8.9, 10.2, 14.3, 14.7, 15.4, 17.1, 18.8, 19.5, 20.9, 22.5 and 23.8 (±0.2θ).

Form B of the mono-sulfate salt can also be characterized by the X-ray powder diffraction pattern shown on FIG. 4.

Form B of the mono-sulfate salt can also be characterized by an infrared spectrum having sharp bands at 3122, 3039, 3003, 2923, 2853, 2719, 2608, 2231, 1622, 1585, 1565, 1515, 1439, 1373, 1346, 1224, 1158, 1116, 1082, 1047, 1015, 987, 901, 787, and 673 (±3 $cm^{-1}$).

Form B of the mono-sulfate salt can also be characterized by the infrared spectrum shown on FIG. 5.

Form B of the mono-sulfate salt is a monohydrate with a corresponding weight loss in the TGA curve as shown on FIG. 6.

As mentioned hereinabove, all these characteristics are shown on FIGS. 4 to 6 hereinafter.

A room temperature single crystal X-ray analysis of form B of the mono-sulfate salt was conducted. As an example table 2 lists some crystal structure data.

Form B of the mono-sulfate salt was found to be a monohydrate of the mono-sulfate salt as determined by single crystal analysis. The experimental XRPD pattern collected with the form B of the mono-sulfate salt obtained is in excellent agreement with the simulated pattern calculated with atomic coordinates from single crystal structure analysis, indicating that form B of the mono-sulfate salt was a pure crystalline phase. In the structure of form B of 2-Chloro-4-[1-(4-fluoro-phenyl)-2,5-dimethyl-1H-imidazol-4-ylethynyl]-pyridine, the dihedral angle between the fluoro-benzene ring and the imidazole ring was found to be approximately 77.3°. The protonated imidazole nitrogen atom forms an intermolecular hydrogen bond with a bisulfate anion. At the same time, the bisulfate anion is also involved in hydrogen bonding networks with a chloro-pyridine nitrogen atom and a water molecule.

TABLE 1 crystal structure data of form A of the mono-sulfate salt

| Name | Form A of the mono-sulfate salt | |
|---|---|---|
| Temperature | 293(2) K | |
| Crystal system, space group | Triclinic, P-1 | |
| Unit cell dimensions | a = 9.996(2) Å | α = 98.60(3)° |
| | b = 9.996(2) Å | β = 98.97(3)° |
| | c = 11.287(2) Å | γ = 112.49(3)° |
| Cell volume | 1001.9(3) Å³ | |
| Molecules in unit cell | 2 | |
| Density (calculated) | 1.398 g/cm³ | |

TABLE 2

Crystal structure data and structure refinement for form B of the mono-sulfate salt

| Name | Form B of the mono-sulfate salt | |
|---|---|---|
| Temperature | 294(2) K | |
| Crystal system, Space group | Triclinic, P-1 | |
| Unit cell dimensions | a = 8.9686(5) Å | α = 107.0630(10)° |
| | b = 10.6790(6) Å | β = 100.1590(10)°. |
| | c = 10.9563(6) Å | γ = 96.6930(10)° |
| Cell volume | 971.51(9) Å³ | |
| molecules in unit cell | 2 | |
| Density (calculated) | 1.510 g/cm³ | |

The amorphous form of mono-sulfate salt of 2-Chloro-4-[1-(4-fluoro-phenyl)-2,5-dimethyl-1H-imidazol-4-ylethynyl]-pyridine can be obtained from a methanol solution upon fast evaporation at about 65° C. under vacuum.

The amorphous form of mono-sulfate salt can be characterized by the lack of sharp X-ray diffraction peaks in its XRPD pattern; and/or an infrared spectrum having sharp bands at 2730, 2592, 2219, 1633, 1586, 1570, 1513, 1375, 1343, 1293, 1226, 1157, 1130, 1084, 1040, 986, 903, 848, 788, 712 and 670 cm$^{-1}$ ($\pm 3$ cm$^{-1}$).

The amorphous form of mono-sulfate salt can also be characterized by the infrared spectrum shown on FIG. 11.

As mentioned hereinabove, all these characteristics are shown on FIGS. 10 to 11 hereinafter.

The hemi-sulfate salt of 2-Chloro-4-[1-(4-fluoro-phenyl)-2,5-dimethyl-1H-imidazol-4-ylethynyl]-pyridine can be prepared by solvent equilibration of form A of the mono-sulfate salt in water.

Form A of the hemi-sulfate salt can be obtained by solvent equilibration of form A of the mono-sulfate salt in water. It can also be prepared by re-crystallization or digestion of form A of the mono-sulfate salt in solvent systems comprising but not limited to water, water/methanol (e.g. 4:1, v/v), water/ethanol (e.g. 4:1, v/v), water/2-propanol (e.g. 3:1, v/v).

Form A of the hemi-sulfate salt is a crystalline hemi-hydrate form of the following salt of 2-Chloro-4-[1-(4-fluoro-phenyl)-2,5-dimethyl-1H-imidazol-4-ylethynyl]-pyridine with sulfuric acid (2:1) (hemi sulfate salt of the 2-Chloro-4-[1-(4-fluoro-phenyl)-2,5-dimethyl-1H-imidazol-4-ylethynyl]-pyridine free base):

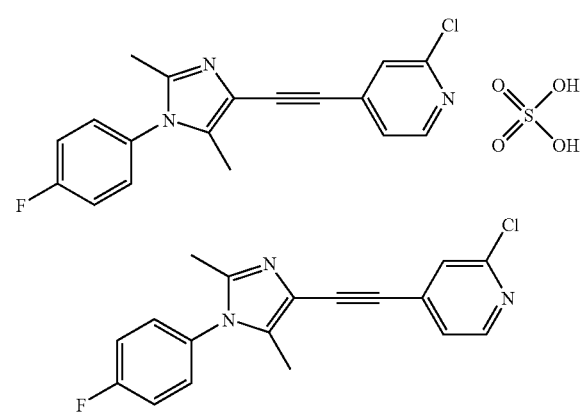

Form of the hemi-sulfate salt can be characterized by at least three peaks selected from the following X-ray diffraction peaks obtained with a Cu$_{K\alpha}$ radiation at 2θ (2 Theta)=7.4, 8.9, 11.0, 11.8, 12.8, 15.8, 17.3, 18.1, 19.8, 25.0 and 26.2 ($\pm 0.2°$).

Form of the hemi-sulfate salt can also be characterized by the following X-ray diffraction peaks obtained with a Cu$_{K\alpha}$ radiation at 2θ (2 Theta)=7.4, 8.9, 11.0, 11.8, 12.8, 15.8, 17.3, 18.1, 19.8, 25.0 and 26.2 ($\pm 0.2°$).

Form of the hemi-sulfate salt can also be characterized by the X-ray powder diffraction pattern shown on FIG. 7.

Form of the hemi-sulfate salt can also be characterized by an infrared spectrum having sharp bands at 3364, 3075, 3004, 2922, 2851, 2717, 2208, 1658, 1632, 1585, 1567, 1514, 1413, 1372, 1159, 1122, 1038, 986, 902, 846, 821, 788, 721, 712, and 668 ($\pm 3$ cm$^{-1}$).

Form of the hemi-sulfate salt can also be characterized by the infrared spectrum shown on FIG. 8.

Form A of the hemi-sulfate salt is a hemi-hydrate with a corresponding weight loss in the TGA curve as shown on FIG. 9.

As already mentioned hereinabove, all these characteristics are shown on FIGS. 7 to 9 hereinafter.

A low and room temperature single crystal X-ray analysis of form A of the hemi-sulfate salt was conducted. Table 3 lists as an example some crystal structure data.

Form A of the hemi-sulfate salt was found to be a hemi-hydrate of the hemisulfate as determined by single crystal structure analysis. In the structure of form A of the hemi-sulfate salt, there are two API molecules in the asymmetric unit. The experimental XRPD pattern collected was consistent with the simulated pattern calculated with atomic coordinates from single crystal structure analysis, indicating a pure crystalline phase. The conformations of these two API molecules are slightly different as indicated by the dihedral angle differences between the fluoro-benzene ring and the imidazole ring (approximately 70° vs approximately 61°); however, in both molecules, the chloro-pyridine rings are almost co-planer to the imidazole ring as demonstrated by very small dihedral angles (approximately 5° vs approximately 6°). The protonated imidazole nitrogen atoms form intermolecular hydrogen bonds with a sulfate anion and a water molecule. At the same time, the water molecule is also involved in hydrogen bonding with two sulfate anions.

TABLE 3

Crystal structure data and structure refinement for form A of the hemi-sulfate salt

| Name | Form A of the hemi-sulfate salt | |
|---|---|---|
| Temperature | 294(2) K | |
| Crystal system, Space group | Monoclinic, C2/c | |
| Unit cell dimensions | a = 18.3260(13) Å | α = 90° |
|  | b = 17.0770(12) Å | β = 109.002(1)° |
|  | c = 25.1530(18) Å | γ = 90° |
| Cell volume | 7442.8(9) Å$^3$ | |
| molecules in unit cell | 8 | |
| Density (calculated) | 1.370 Mg/m$^3$ | |

The salt can be formulated at low or high concentrations in a composition further comprising usual pharmaceutically acceptable adjuvants known in the art.

The present invention also provides pharmaceutical compositions containing one or more of the following species:
- a mono- or hemi-sulfate salt of 2-Chloro-4-[1-(4-fluoro-phenyl)-2,5-dimethyl-1H-imidazol-4-ylethynyl]-pyridine;
- form A or B of the mono-sulfate salt of 2-Chloro-4-[1-(4-fluoro-phenyl)-2,5-dimethyl-1H-imidazol-4-ylethynyl]-pyridine;
- form A of the hemi-sulfate salt of 2-Chloro-4-[1-(4-fluoro-phenyl)-2,5-dimethyl-1H-imidazol-4-ylethynyl]-pyridine;
- the amorphous form of 2-Chloro-4-[1-(4-fluoro-phenyl)-2,5-dimethyl-1H-imidazol-4-ylethynyl]-pyridine.

and a pharmaceutically acceptable carrier.

These pharmaceutical compositions can be in the form of tablets, coated tablets, dragees, hard and soft gelatine capsules, solutions, emulsions or suspensions. The invention also provides a process for the production of such compositions, which comprises bringing the aforementioned modifications and forms into a galenical administration form together with one or more therapeutically inert carriers.

In addition, the pharmaceutical compositions can contain pharmaceutically acceptable preservatives, solubilizers, stabilizers, wetting agents, emulsifiers, sweeteners, colorants, flavoring agents, salts for varying the osmotic pressure, buffers, masking agents or antioxidants. They can also contain still other therapeutically valuable substances.

In accordance with the invention, the salts, crystalline or amorphous forms according to the invention mentioned hereinabove can be used for the preparation of medicaments useful in the treatment or prevention of illnesses in which the mGluR5 receptors play a role. Such illnesses include acute and/or chronic neurological disorders, in particular anxiety, or for the treatment of chronic and acute pain, protection against liver damage, failure whether drug or disease induced, urinary incontinence, obesity, Fragile-X or Autism.

The salts and crystalline and amorphous forms of the compounds of the invention can be used in method of treating an illness selected from the group consisting of acute and/or chronic neurological disorders, in particular anxiety, or for the treatment of chronic and acute pain, protection against liver damage, failure whether drug or disease induced, urinary incontinence, obesity, Fragile-X or Autism, which method comprises administering to an individual an effective amount of one species selected from the group consisting of the salts, crystalline or amorphous forms according to the invention mentioned hereinabove.

The dosage at which the salts, crystalline or amorphous forms according to the invention are administered can vary within wide limits and will, of course, have to be adjusted to the individual requirements in each particular case. In the case of oral administration the dosage for adults can vary from about 0.01 mg to about 1000 mg, preferably from about 0.05 mg to about 20 mg, and still more preferably from about 0.5 mg to about 5 mg per day. The daily dosage may be administered as single dose or in divided doses and, in addition, the upper limit can also be exceeded when this is found to be indicated.

EXAMPLE 1

Preparation of Form A of the Mono-sulfate Salt of 2-Chloro-4-[1-(4-fluoro-phenyl)-2,5-dimethyl-1H-imidazol-4-ylethynyl]-pyridine General Form A of the mono-sulfate salt of 2-chloro-4-[1-(4-fluoro-phenyl)-2,5-dimethyl-1H-imidazol-4-ylethynyl]-pyridine can be formed upon salt formation with or without seeding with form A of the mono-sulfate salt in an appropriate solvent system as e.g. 2-propanol/water, or by re-crystallization of form A of the mono-sulfate salt in solvents comprising but not limited to acetonitrile, acetonitrile/water, methanol, ethanol, 2-propanol, acetic acid, 1-octanol, 2-propanol/49% sulfuric acid (10:1, v/v).

Preparation Procedure 61.0 g of 2-chloro-4-[1-(4-fluoro-phenyl)-2,5-dimethyl-1H-imidazol-4-ylethynyl]-pyridine was dissolved in 610 mL of 2-propanol. The solution was filtered and the filter rinsed with 31 mL of 2-propanol. To the combined solutions a mixture of 30 mL of water and 18.91 g of sulfuric acid (97%) was added drop-wise. The solution was cooled to 0-5° C. Seeding was performed at 58° C. as needed. The solid residues were filtered, washed with 2-propanol (0-5° C.) and dried at 50° C./<1 mbar for 18 h. Yield: 69.1 g (87.1%).

Form A seeding crystals can be prepared upon cooling crystallization of a hot solution of 250 mg of the mono-sulfate salt of 2-chloro-4-[1-(4-fluoro-phenyl)-2,5-dimethyl-1H-imidazol-4-ylethynyl]-pyridine in 10 ml of 2-propanol. After cooling to 0° C. the solid residues can be filtered and dried at 50° C. under vacuum.

Solid State Properties of Form A of the Mono-sulfate Salt

XRPD-pattern, IR-spectrum and TGA-curve of a typical lot of form A of the mono-sulfate salt are listed in FIGS. 1 to 3.

EXAMPLE 2

Preparation of Form B of the Mono-sulfate Salt of 2-Chloro-4-[1-(4-fluoro-phenyl)-2,5-dimethyl-1H-imidazol-4-ylethynyl]-pyridine General Form B of the mono-sulfate salt of 2-chloro-4-[1-(4-fluoro-phenyl)-2,5-dimethyl-1H-imidazol-4-ylethynyl]-pyridine can be produced by solvent equilibration of form A of the mono-sulfate salt in solvent systems as e.g. 2-propanol/water or 1 N sulfuric acid, or upon seeded cooling crystallization of the mono-sulfate salt of 2-chloro-4-[1-(4-fluoro-phenyl)-2,5-dimethyl-1H-imidazol-4-ylethynyl]-pyridine in solvent systems as e.g. 2-propanol/water.

Preparation Procedure 300 mg of form A of the mono-sulfate salt of 2-chloro-4-[1-(4-fluoro-phenyl)-2,5-dimethyl-1H-imidazol-4-ylethynyl]-pyridine was dissolved in 3 ml 2-propanol and 1 ml water at 60° C. to produce a clear solution. The clear solution was seeded with form B of the mono-sulfate salt and sealed at room temperature. Single crystals were formed after 3 days.

Seeding crystals can be prepared by formation of a saturated slurry of form A of the mono-sulfate salt of 2-chloro-4-[1-(4-fluoro-phenyl)-2,5-dimethyl-1H-imidazol-4-ylethynyl]-pyridine in 2-propanol and water (3:1 v/v) at room temperature. The slurry was stirred at room temperature for approximately 3 weeks. The solids were filtered via a glass filter to afford crystalline form B of the mono-sulfate salt as a wet cake.

Solid State Properties of Form B of the Mono-sulfate Salt

XRPD-pattern, IR-spectrum and TGA-curve of a typical lot of form B of the mono-sulfate salt are listed in FIGS. 4 to 6.

EXAMPLE 3

Preparation of Form A of the Hemi-sulfate Salt of 2-Chloro-4-[1-(4-fluoro-phenyl)-2,5-dimethyl-1H-imidazol-4-ylethynyl]-pyridine General Form A of the hemi-sulfate salt of 2-chloro-4-[1-(4-fluoro-phenyl)-2,5-dimethyl-1H-imidazol-4-ylethynyl]-pyridine can be produced by solvent equilibration of form A of the mono-sulfate salt in solvents as e.g. water. It can also be prepared by re-crystallization or digestion of form A of the mono-sulfate salt in solvent systems comprising but not limited to water, water/methanol (e.g. 4:1, v/v), water/ethanol (e.g. 4:1, v/v), water/2-propanol (e.g. 3:1, v/v).

Preparation Procedure 41 g of form A of the Mono-sulfate of 2-chloro-4-[1-(4-fluoro-phenyl)-2,5-dimethyl-1H-imidazol-4-ylethynyl]-pyridine was mixed with 128 g of water. The slurry was stirred at room temperature for 2-16 h. After all the form A of the mono-sulfate salt had been converted to the hemi sulfate salt the crystals were collected by filtration and rinsed with water. The wet cake was dried at 40° C. in a vacuum oven for 48 hrs. The yield was ~93%.

Solid State Properties of Form A of the Hemi-sulfate Salt

XRPD-pattern, IR-spectrum and TGA-curve of a typical lot of form A of the hemi-sulfate salt are listed in FIGS. 7 to 9.

EXAMPLE 4

Preparation of the Amorphous Form of the Mono-sulfate Salt of 2-Chloro-4-[1-(4-fluoro-phenyl)-2,5-dimethyl-1H-imidazol-4-ylethynyl]-pyridine Formation of the Amorphous Form Amorphous mono-sulfate salt of 2-Chloro-4-[1-(4-fluoro-phenyl)-2,5-dimethyl-1H-imidazol-4-ylethynyl]-pyridine is accessible upon fast evaporation of a solution in an a appropriate solvent, preferably methanol.

Fast Evaporation 0.53 g of 2-Chloro-4-[1-(4-fluoro-phenyl)-2,5-dimethyl-1H-imidazol-4-ylethynyl]-pyridine was dissolved in 10 mL of methanol at approximately 65° C. After complete evaporation of the solvent under vacuum, the solid (foam) was further dried at ca. 50° C./5-20 mbar for 18 h. Analysis revealed amorphous 2-Chloro-4-[1-(4-fluoro-phenyl)-2,5-dimethyl-1H-imidazol-4-ylethynyl]-pyridine.

Solid State Properties of the Amorphous Form

XRPD-pattern and IR-spectrum of the amorphous form are listed in FIGS. 10 to 11.

Formulation

| | | Capsule Formulation (Wet granulation) | | | |
|---|---|---|---|---|---|
| | | | mg/capsule | | |
| Item | Ingredients | 0.05 mg | 0.5 mg | 2.0 mg | 20.0 mg |
| 1. | Form A of monosulfate salt | 0.065 | 0.650 | 2.602 | 26.02 |
| 2. | Lactose Monohydrate | 108.934 | 109.349 | 107.398 | 83.98 |
| 3. | Starch Maize Partially Pregelatinized (type 1500) | 60.00 | 60.00 | 60.00 | 60.00 |
| 4. | Croscarmellose Sodium | 8.00 | 8.00 | 8.00 | 8.00 |
| 5. | Povidone 30 | 15.00 | 15.00 | 15.00 | 15.00 |
| 6. | Sodium lauryl sulfate | 1.00 | — | — | — |
| 7. | Talc | 6.00 | 6.00 | 6.00 | 6.00 |
| 8. | Magnesium Stearate | 1.00 | 1.00 | 1.00 | 1.00 |
| | Total | 200.00 | 200.00 | 200.00 | 200.00 |

Manufacturing Procedure
1. Mix items 1, 2, 3, 4, 5 and 6 in a suitable mixer for 30 minutes.
2. Add items 7 and 8 and mix for 3 minutes.
3. Fill into a suitable capsule.

The invention claimed is:

1. A mono-sulfate salt of 2-Chloro-4-[1-(4-fluoro-phenyl)-2,5-dimethyl-1H-imidazol-4-ylethynyl]-pyridine.

2. A crystalline form of the mono-sulfate salt of 2-Chloro-4-[1-(4-fluoro-phenyl)-2,5-dimethyl-1H-imidazol-4-ylethynyl]-pyridine characterized by at least three peaks selected from the following X-ray diffraction peaks obtained with a $Cu_{K\alpha}$ radiation at 2θ (2 Theta)=9.8, 13.4, 14.2, 18.1, 18.9, 19.6, 22.6, 22.9, 25.7, 27.1 and 29.9 (±0.2°).

3. A crystalline form of the mono-sulfate salt of 2-Chloro-4-[1-(4-fluoro-phenyl)-2,5-dimethyl-1H-imidazol-4-ylethynyl]-pyridine characterized the following X-ray diffraction peaks obtained with a $Cu_{K\alpha}$ radiation at 2θ (2 Theta)=9.8, 13.4, 14.2, 18.1, 18.9, 19.6, 22.6, 22.9, 25.7, 27.1 and 29.9 (±0.2°).

4. A crystalline form of the mono-sulfate salt of 2-Chloro-4-[1-(4-fluoro-phenyl)-2,5-dimethyl-1H-imidazol-4-ylethynyl]-pyridine characterized by the X-ray powder diffraction pattern shown on FIG. 1.

5. A crystalline form of the mono-sulfate salt of 2-Chloro-4-[1-(4-fluoro-phenyl)-2,5-dimethyl-1H-imidazol-4-ylethynyl]-pyridine according to claim 1 characterized by an infrared spectrum having sharp bands at 3068, 2730, 2618, 2236, 2213, 1628, 1587, 1569, 1518, 1384, 1374, 1295, 1236, 1168, 1157, 1116, 1064, 1019, 902, 855, 786 and 674 cm$^{-1}$ (±3 cm$^{-1}$).

6. A crystalline form of the mono-sulfate salt of 2-Chloro-4-[1-(4-fluoro-phenyl)-2,5-dimethyl-1H-imidazol-4-ylethynyl]-pyridine according to claim 1 characterized by the infrared spectrum shown on FIG. 2.

7. A pharmaceutical composition comprising the Form A mono-sulfate salt of 2-Chloro-4-[1-(4-fluoro-phenyl)-2,5-dimethyl-1H-imidazol-4-ylethynyl]-pyridine wherein the composition has the following formulation:

| | mg/capsule 0.05 mg |
|---|---|
| Form A of monosulfate salt | 0.065 |
| Lactose Monohydrate | 108.934 |
| Starch Maize Partially Pregelatinized (type 1500) | 60.00 |
| Croscarmellose Sodium | 8.00 |
| Povidone 30 | 15.00 |
| Sodium lauryl sulfate | 1.00 |
| Talc | 6.00 |
| Magnesium Stearate | 1.00 |
| Total | 200.00. |

8. A pharmaceutical composition comprising the Form A mono-sulfate salt of 2-Chloro-4-[1-(4-fluoro-phenyl)-2,5-dimethyl-1H-imidazol-4-ylethynyl]-pyridine wherein the composition has the following formulation:

| | mg/capsule 0.5 mg |
|---|---|
| Form A of monosulfate salt | 0.650 |
| Lactose Monohydrate | 109.349 |
| Starch Maize Partially Pregelatinized (type 1500) | 60.00 |
| Croscarmellose Sodium | 8.00 |
| Povidone 30 | 15.00 |
| Sodium lauryl sulfate | — |
| Talc | 6.00 |
| Magnesium Stearate | 1.00 |
| Total | 200.00. |

9. A pharmaceutical composition comprising the Form A mono-sulfate salt of 2-Chloro-4-[1-(4-fluoro-phenyl)-2,5-dimethyl-1H-imidazol-4-ylethynyl]-pyridine wherein the composition has the following formulation:

10. A pharmaceutical composition comprising the Form A mono-sulfate salt of 2-Chloro-4-[1-(4-fluoro-phenyl)-2,5-dimethyl-1H-imidazol-4-ylethynyl]-pyridine wherein the composition has the following formulation:

|  | mg/capsule 2.0 mg |
|---|---|
| Form A of monosulfate salt | 2.602 |
| Lactose Monohydrate | 107.398 |
| Starch Maize Partially Pregelatinized (type 1500) | 60.00 |
| Croscarmellose Sodium | 8.00 |
| Povidone 30 | 15.00 |
| Sodium lauryl sulfate | — |
| Talc | 6.00 |
| Magnesium Stearate | 1.00 |
| Total | 200.00. |

|  | mg/capsule 20.0 mg |
|---|---|
| Form A of monosulfate salt | 26.02 |
| Lactose Monohydrate | 83.98 |
| Starch Maize Partially Pregelatinized (type 1500) | 60.00 |
| Croscarmellose Sodium | 8.00 |
| Povidone 30 | 15.00 |
| Sodium lauryl sulfate | — |
| Talc | 6.00 |
| Magnesium Stearate | 1.00 |
| Total | 200.00. |

\* \* \* \* \*